US011304611B2

(12) United States Patent
Fukunishi et al.

(10) Patent No.: US 11,304,611 B2
(45) Date of Patent: Apr. 19, 2022

(54) IMAGE PROCESSING APPARATUS, IMAGE PROCESSING METHOD, AND COMPUTER READABLE RECORDING MEDIUM

(71) Applicants: OLYMPUS CORPORATION, Hachioji (JP); NATIONAL UNIVERSITY CORPORATION CHIBA UNIVERSITY, Chiba (JP)

(72) Inventors: Munenori Fukunishi, Kunitachi (JP); Norimichi Tsumura, Chiba (JP); Koki Kurita, Chiba (JP)

(73) Assignees: OLYMPUS CORPORATION, Tokyo (JP); NATIONAL UNIVERSITY CORPORATION CHIBA UNIVERSITY, Chiba (JP)

(*) Notice: Subject to any disclaimer, the term of this patent is extended or adjusted under 35 U.S.C. 154(b) by 192 days.

(21) Appl. No.: 16/724,016

(22) Filed: Dec. 20, 2019

(65) Prior Publication Data
US 2020/0121192 A1  Apr. 23, 2020

Related U.S. Application Data

(63) Continuation of application No. PCT/JP2017/023458, filed on Jun. 26, 2017.

(51) Int. Cl.
*G06K 9/00* (2022.01)
*A61B 5/021* (2006.01)
(Continued)

(52) U.S. Cl.
CPC .............. *A61B 5/021* (2013.01); *A61B 5/489* (2013.01); *G06T 7/0012* (2013.01); *G06T 2207/30101* (2013.01)

(58) Field of Classification Search
CPC ...................................... A61B 5/021
See application file for complete search history.

(56) References Cited

U.S. PATENT DOCUMENTS 8,897,522 B2  11/2014  Mestha et al.
2011/0301447 A1*  12/2011  Park ................. G06T 7/0016
                                                                   600/407
(Continued)

FOREIGN PATENT DOCUMENTS

JP           4756398 B2    12/2009
JP        2010268979 A    12/2010
(Continued)

OTHER PUBLICATIONS

International Search Report (ISR) dated Sep. 19, 2017 (and English translation thereof), issued in International Application No. PCT/JP2017/023458.
(Continued)

*Primary Examiner* — Oneal R Mistry
(74) *Attorney, Agent, or Firm* — Holtz, Holtz & Volek PC

(57) ABSTRACT

An image processing apparatus includes a processor including hardware. The processor is configured to: acquire video data; estimate a spatial distribution of a predetermined biological component for which a component spectrum temporally varies with respect to image data of a predetermined frame among a plurality of frames included in the video data; generate biological component video data in which the biological component is extracted from the video data based on the estimated spatial distribution of the biological component in the image data of the predetermined frame; and generate periodic variation video data of the biological component by applying, to the biological component video data, a filter for extracting a predetermined frequency component.

8 Claims, 14 Drawing Sheets

(51) Int. Cl.
*A61B 5/00* (2006.01)
*G06T 7/00* (2017.01)

(56) References Cited

U.S. PATENT DOCUMENTS

| | | | | |
|---|---|---|---|---|
| 2012/0075447 | A1* | 3/2012 | Iwane | A61B 1/05 |
| | | | | 348/65 |
| 2017/0032702 | A1* | 2/2017 | Goksel | G09B 23/286 |
| 2017/0035268 | A1* | 2/2017 | Kumar | G06T 15/80 |
| 2017/0042428 | A1* | 2/2017 | Kellnberger | A61B 5/7257 |
| 2017/0061687 | A1* | 3/2017 | Hong | G06F 3/04845 |
| 2017/0079741 | A1* | 3/2017 | Makinouchi | A61B 90/00 |
| 2017/0100024 | A1* | 4/2017 | Shah | A61B 1/0017 |

FOREIGN PATENT DOCUMENTS

| | | |
|---|---|---|
| JP | 2012205855 A | 10/2012 |
| JP | 2013248386 A | 12/2013 |

OTHER PUBLICATIONS

Written Opinion of the International Searching Authority dated Sep. 19, 2017 issued in International Application No. PCT/JP2017/023458.

Balakrishnan, et al., "Detecting Pulse from Head Motions in Video", Computer Vision and Pattern Recognition (CVPR), 2013 IEEE Conference on IEEE, pp. 3430-3437.

Kioi, et al., "Feasibility Study on Visualization of Hemoglobin Concentration Using the Near-infrared Spectral Reflectance Motion-Image", Transactions of the Visualization Society of Japan, Oct. 2011, vol. 31, No. 10, pp. 57-61.

Wang, et al., "Algorithmic principles of remote-PPG", IEEE Transactions on Biomedical Engineering, Sep. 13, 2016, pp. 1479-1491, accessed online <https://ieeexplore.ieee.org/document/7565547>.

* cited by examiner

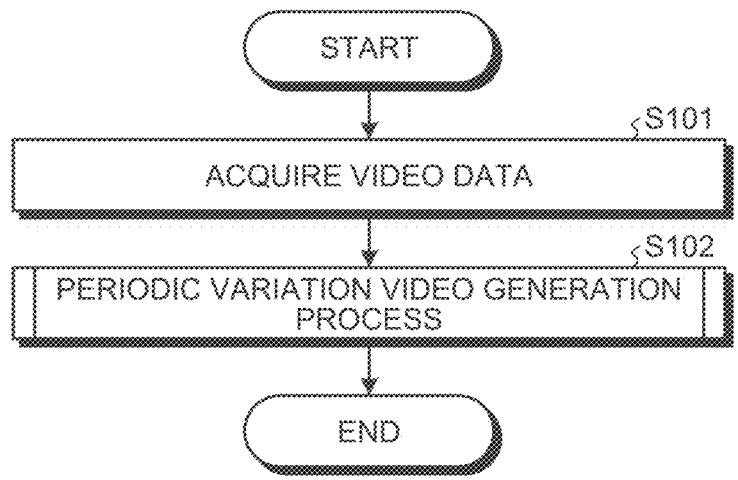
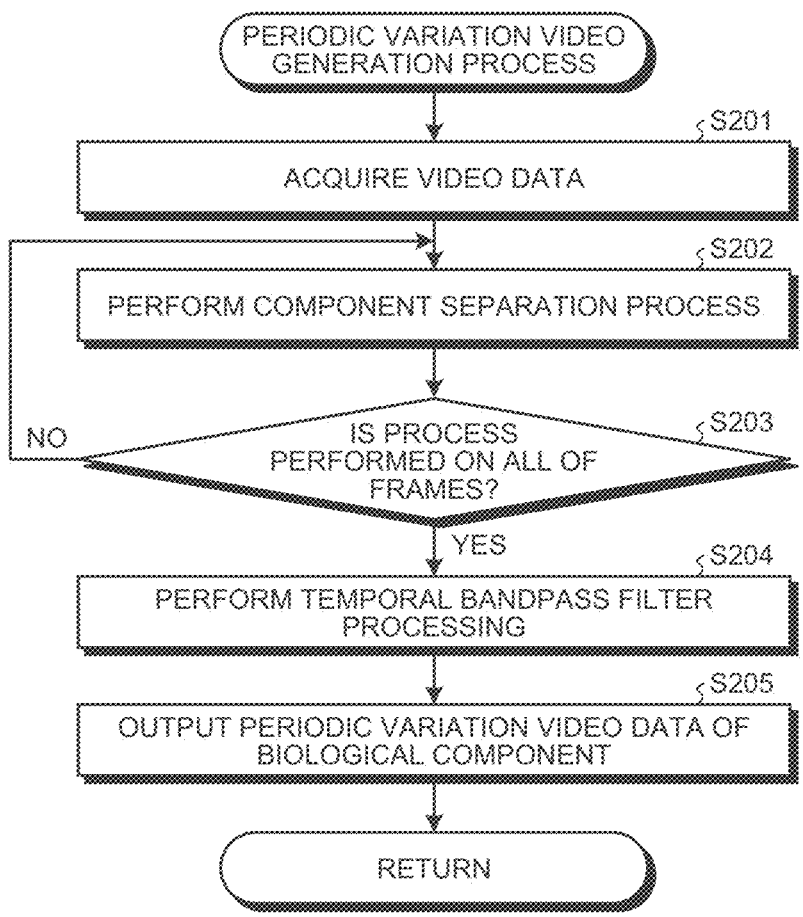

R1    R2

US 11,304,611 B2

IMAGE PROCESSING APPARATUS, IMAGE PROCESSING METHOD, AND COMPUTER READABLE RECORDING MEDIUM

This application is a continuation of International Application No. PCT/JP2017/023458, filed on Jun. 26, 2017, the entire contents of which are incorporated herein by reference.

BACKGROUND

The present disclosure relates to an image processing apparatus, an image processing method, and a computer readable recording medium.

In surgery or endoscopic surgery, a doctor performs procedures while confirming positions of blood vessels. If a blood vessel is located near a biological surface, such as a mucosa or a surface of an organ, which is to be operated, the doctor is able to visually recognize presence of the blood vessel without any difficulty, but if a blood vessel is located in a layer below the biological surface, it is difficult to visually recognize the blood vessel from the surface, leading to difficulties. If a blood vessel is located in a layer below the biological surface, the doctor may perform procedures while confirming beats of the biological surface, or the doctor may perform procedures while estimating arrangement of blood vessels based on anatomical knowledge, that is, at present, the doctor relies on his/her own rules of thumb. Therefore, in surgery or endoscopic surgery, if it becomes possible to output, through video analysis, arrangement of blood vessels or the like that is not easily viewable from the biological surface, it may become possible to reduce burden on the doctor.

In recent years, with the development of a video processing technology, a video magnification method of enhancing subtle motions and color changes included in videos has been proposed (see G. Balakrishnan, F. Durand, and J. Guttag, "Detecting pulse from head motions in video," in Computer Vision and Pattern Recognition (CVPR), 2013 IEEE Conference on. IEEE, 2013, pp. 3430-3437). In this method, a blurred video is generated by applying a spatial low-pass filter to each of frames of a video, a temporal bandpass filter is applied to the blurred video to extract a variation component at a desired frequency, and the extracted variation component is synthesized with an input video while multiplying the extracted variation component by a gain, so that an output image in which local variation appears is obtained. With this method, it is possible to visualize subtle variation that can hardly be visually recognized by a human being, and it is possible to provide a clue to recognition of presence or absence of a blood vessel in a layer below the biological surface.

SUMMARY

According to one aspect of the present disclosure, there is provided an image processing apparatus including a processor including hardware, the processor being configured to: acquire video data; estimate a spatial distribution of a predetermined biological component for which a component spectrum temporally varies with respect to image data of a predetermined frame among a plurality of frames included in the video data; generate biological component video data in which the biological component is extracted from the video data based on the estimated spatial distribution of the biological component in the image data of the predetermined frame; and generate periodic variation video data of the biological component by applying, to the biological component video data, a filter for extracting a predetermined frequency component.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a flowchart illustrating an outline of processing performed by an image processing apparatus according to the first embodiment;

FIG. 3 is a flowchart illustrating an outline of a periodic variation video generation process in FIG. 2;

DETAILED DESCRIPTION

Modes (hereinafter, referred to as "embodiments") for carrying out the present disclosure will be described below. In the embodiments, an imaging system that consecutively captures images of a subject, such as a patient, to generate video data and displays the video data will be described as an example. Further, the present disclosure is not limited by the embodiments below. Furthermore, in description of the drawings, the same components are denoted by the same reference symbols.

Configuration of Imaging System

Figure 1:
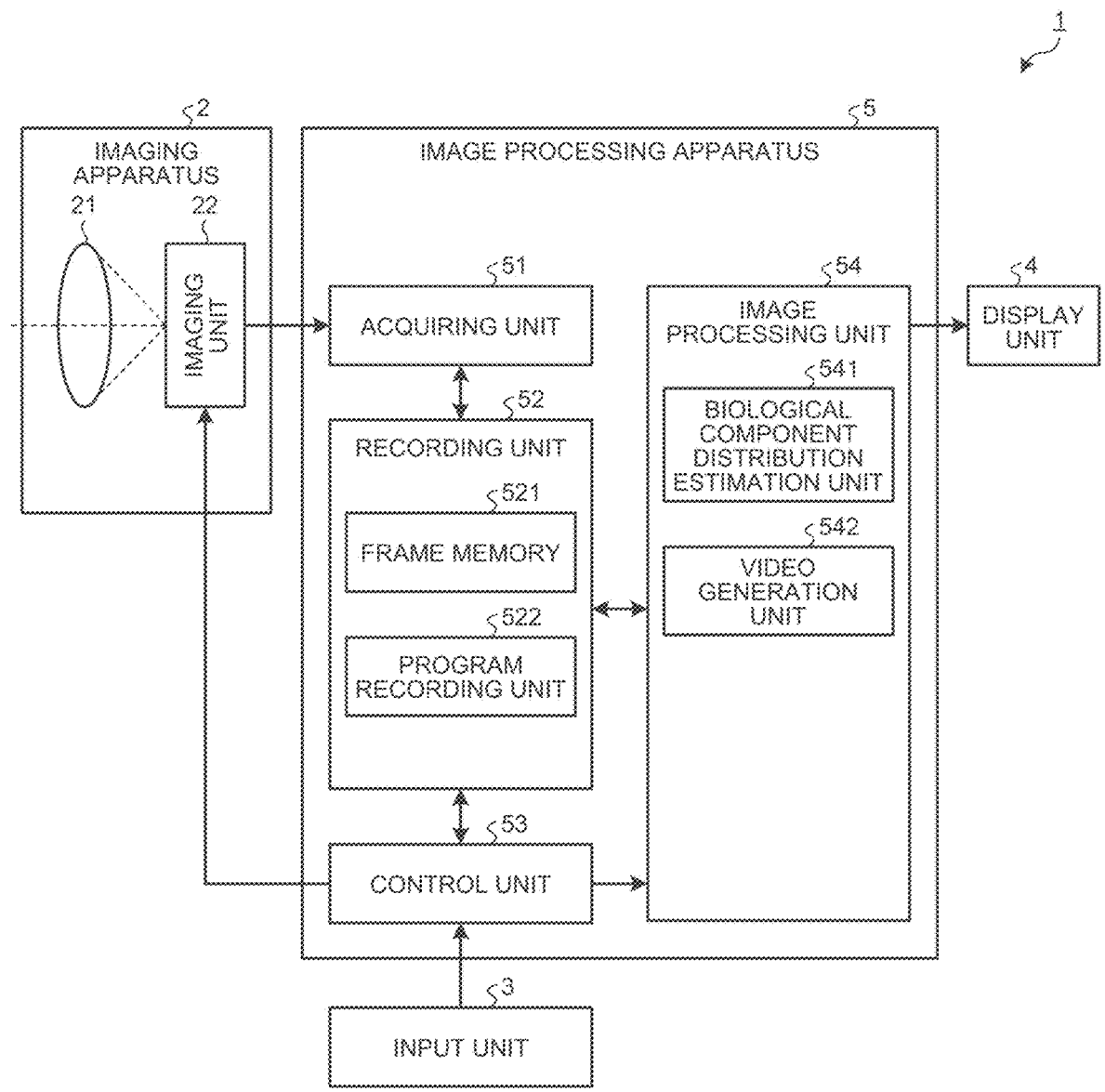
FIG. 1 is a block diagram illustrating a functional configuration of an imaging system according to a first embodiment.

FIG. 1 is a block diagram illustrating a functional configuration of an imaging system according to a first embodiment. An imaging system 1 illustrated in FIG. 1 is a system that displays, in an emphasized manner, local and subtle variation that is caused by a living body and that is included in a video corresponding to video data that is generated by consecutively capturing images of a subject, such as a patient. As illustrated in FIG. 1, the imaging system 1 includes an imaging apparatus 2 that generates video data constructed of frames of temporally-consecutive pieces of image data obtained by capturing images of the subject, an input unit 3 that receives input of various kinds of operation information on the imaging system 1, a display unit 4 that displays various kinds of information on the imaging system 1 and videos corresponding to video data, and an image processing apparatus 5 that acquires the video data generated by the imaging apparatus 2, performs predetermined image processing on the video data, and outputs the video data to the display unit 4.

First, the imaging apparatus 2 will be described.

As illustrated in FIG. 1, the imaging apparatus 2 includes an optical system 21 and an imaging unit 22.

The optical system 21 is constituted by one or more lenses and has a zoom function to change a focal distance and a focus function to change a focal position. The optical system 21 collects light of a subject image and forms the subject image on a light receiving surface of the imaging unit 22.

The imaging unit 22 generates video data by consecutively capturing the subject image formed by the optical system 21 at a predetermined frame rate (for example, 60 fps or 120 fps) under the control of the image processing apparatus 5 to be described later, and outputs the video data to the image processing apparatus 5. The imaging unit 22 is constituted by at least an imaging element, such as a charge coupled device (CCD) or a complementary metal oxide semiconductor (CMOS), that receives the light of the subject image, performs photoelectric conversion, and generates an image signal (electrical signal), a signal processing circuit that performs predetermined signal processing (for example, gain-up processing) on the image signal generated by the imaging element, and an analog-to-digital (A/D) conversion circuit that converts an analog image signal subjected to the signal processing by the signal processing circuit to a digital image signal and outputs the digital image signal as video data or image data.

Next, the input unit 3 will be described.

The input unit 3 receives input of various kinds of operation information on the imaging system 1. Specifically, the input unit 3 receives input of an instruction signal for instructing the imaging apparatus 2 to capture images, input of an instruction signal for giving an instruction to change a gain or color tone of the video data generated by the imaging apparatus 2, input of an instruction signal for giving an instruction to change image processing performed by the image processing apparatus 5, and the like. The input unit 3 is constituted by an input device, such as a keyboard, a mouse, and a touch panel. The input unit 3 need not always be a wired device, but may be a wireless device.

Next, the display unit 4 will be described.

The display unit 4 displays a video corresponding to the video data subjected to image processing by the image processing apparatus 5 or an image corresponding to image data, under the control of the image processing apparatus 5. Further, the display unit 4 displays various kinds of information on the imaging system 1. The display unit 4 is constituted by a display panel using organic electro luminescence, liquid crystal, or the like. The display unit 4 need not always be a wired device, but may be a wireless device.

Next, the image processing apparatus 5 will be described.

The image processing apparatus 5 includes an acquiring unit 51 that acquires the video data generated by the imaging apparatus 2, a recording unit 52 that records therein various programs to be executed by the image processing apparatus 5 and data being processed, a control unit 53 that controls each of the units including the image processing apparatus 5 in the imaging system 1, and an image processing unit 54 that performs image processing on the video data acquired by the acquiring unit 51 and outputs the video data to the display unit 4.

The acquiring unit 51 is appropriately configured in accordance with a mode of the imaging system 1 including the imaging apparatus 2. For example, if a portable recording medium is used to send and receive the video data to and from the imaging apparatus 2, the acquiring unit 51 is configured as a reader device to which the recording medium is detachably attached and which reads the recorded video data. Furthermore, if a server is used to record the video data generated by the imaging apparatus 2, the acquiring unit 51 is configured as a communication device or the like that is able to perform bi-directional communication with the server, and acquires the video data by performing data communication with the server. Moreover, the acquiring unit 51 may be configured as an interface device or the like to which the video data is input from the imaging apparatus 2 via a cable. It is of course possible to configure the acquiring unit 51 as a wireless communication interface device or the like to which the video data is input from the imaging apparatus 2 through wireless communication.

The recording unit 52 is constituted by a flash memory, a synchronous dynamic random access memory (SDRAM), or the like. The recording unit 52 includes a frame memory 521 that temporarily stores therein the video data acquired by the acquiring unit 51, and a program recording unit 522 that records various programs to be executed by the image processing apparatus 5.

The control unit 53 comprehensively controls each of the units of the imaging system 1. The control unit 53 is constituted by a general-purpose processor, such as a central processing unit (CPU), or a dedicated processor, such as various arithmetic circuits including an application specific integrated circuit (ASIC), a field programmable gate arrays (FPGA), and the like that implement specific functions. If the control unit 53 is a general-purpose processor, the control unit 53 reads the various programs stored in the recording unit 52, performs operation of giving instructions and transferring data to each of the units included in the image processing apparatus 5, and comprehensively controls entire operation of the image processing apparatus 5. Further, if the control unit 53 is a dedicated processor, the processor may independently perform various kinds of processing, or the processor and the recording unit 52 may perform various kinds of processing in a cooperative manner or a combined manner by using various kinds of data or the like stored in the recording unit 52.

The image processing unit 54 is constituted by a general-purpose processor, such as a CPU, or a dedicated processor, such as various arithmetic circuits including an ASIC, an FPGA, and the like. The image processing unit 54 acquires the video data from the frame memory 521 of the recording unit 52, performs image processing of displaying, in an emphasized manner, local and subtle variation that is caused by a living body and that is included in a video corresponding to the acquired video data, and outputs the video data to the display unit 4, under the control of the control unit 53. The image processing unit 54 includes a biological component distribution estimation unit 541 and a video generation unit 542.

The biological component distribution estimation unit 541 estimates a spatial distribution of a predetermined biological component for which a component spectrum temporally varies with respect to image data of a predetermined frame among a plurality of frames included in the video data, and generates biological component video data in which the biological component is extracted from the video data based on the estimated spatial distribution of the biological component in each piece of frame image data. Specifically, the biological component distribution estimation unit 541 estimates the spatial distribution of the predetermined biological component for which the component spectrum temporally varies with respect to image data of each of frames or image data of every predetermined number of frames among the plurality of frames included in the video data (for example, image data of every other frame, image data of every 10 frames, or the like), and generates the biological component video data in which the biological component is extracted from the video data based on the estimated spatial distribution of the biological component in the image data of the frames. More specifically, the biological component distribution estimation unit 541 estimates spatial distributions of two or more independent components included in biological components, and generates biological component video data in which the two or more independent components are extracted from the video data. Here, at least one of the biological components is at least one or more of hemoglobin, oxygenated hemoglobin, reduced hemoglobin, bilirubin (hematoidin), porphyrin, and hemosiderin. Meanwhile, at least one of the biological components may be a biological component other than any one or more of melanin, cytochrome, and myoglobin. In the following, the two biological components are assumed as melanin (first independent component) and hemoglobin (second independent component).

The video generation unit 542 generates periodic variation video data of the biological component by applying, to the biological component video data, a filter for extracting a predetermined frequency component. Specifically, the video generation unit 542 generates the periodic variation video data of the biological component by applying, to the biological component video data, a bandpass filter for extracting a predetermined frequency component. Here, frequency characteristic of the bandpass filter is appropriately set depending on the biological components. Specifically, the frequency characteristic of the bandpass filter is set so as to transmit a periodic single based on a physiological phenomenon that varies with a predetermined period. For example, the frequency characteristic of the bandpass filter is set so as to transmit a periodic signal based on at least one or more of heartbeat, a pulse wave, spasm, and breathing of a living body.

Processing Performed by Image Processing Apparatus

Next, processing performed by the image processing apparatus 5 will be described. FIG. 2 is a flowchart illustrating an outline of the processing performed by the image processing apparatus 5.

As illustrated in FIG. 2, first, the acquiring unit 51 acquires the video data from the imaging apparatus 2 (Step S101). In this case, the acquiring unit 51 temporarily records the video data in the frame memory 521 of the recording unit 52.

Subsequently, the image processing unit 54 performs a periodic variation video generation process of generating the biological component video data in which periodic variation of a biological component is extracted from the video data recorded in the frame memory 521 (Step S102). After Step S102, the image processing apparatus 5 terminates the process.

Periodic Variation Video Generation Process

FIG. 3 is a flowchart illustrating an outline of the periodic variation video generation process at Step S102 in FIG. 2.

As illustrated in FIG. 3, first, the biological component distribution estimation unit 541 acquires the video data recorded in the frame memory 521 (Step S201).

Subsequently, the biological component distribution estimation unit 541 performs a component separation process on image data of each of frames included in the video data (Step S202). After Step S202, the image processing apparatus 5 proceeds to Step S203 to be described later.

The component separation process performed by the biological component distribution estimation unit 541 at Step S202 described above will be described in detail below.

The biological component distribution estimation unit 541 performs the component separation process of inputting each of frames included in the video data, i.e., each piece of RGB image data, and acquiring image data of a predetermined component. Here, the RGB image data is color image data having pixel levels (pixel values) corresponding to wavelength components of red (R), green (G), and blue (B) for each of pixel values.

Figure 4:
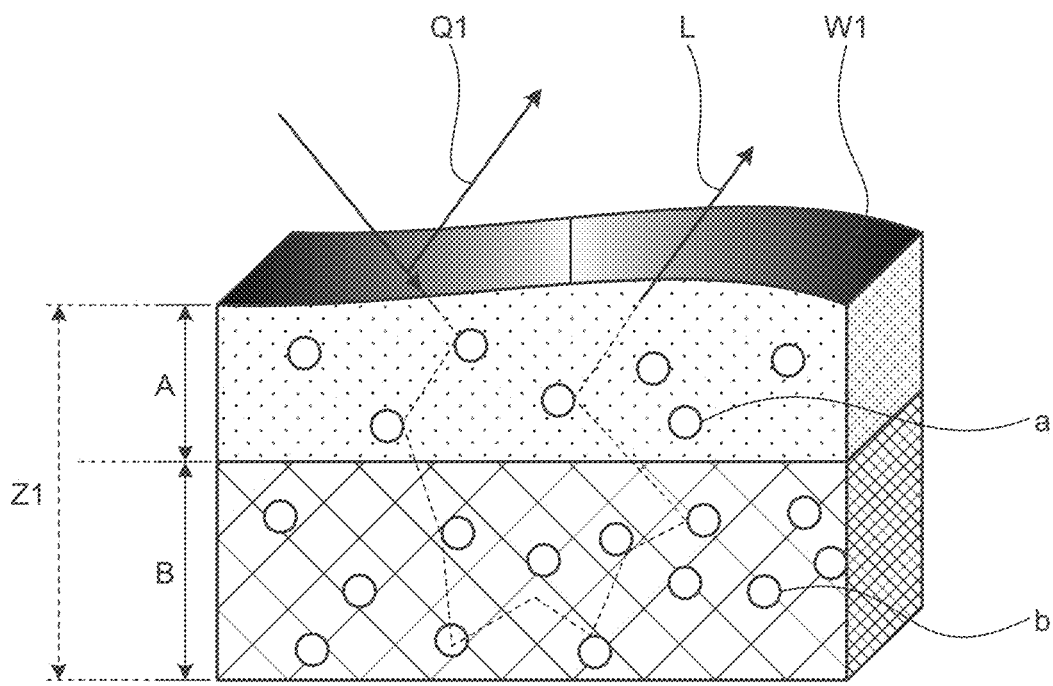
FIG. 4 is a diagram schematically illustrating a cross section of a living body formed of two layers.

Further, as illustrated in FIG. 4, when a surface of a living body Z1 is irradiated with light by a light source (not illustrated), reflected light to be received by the imaging apparatus 2 is classified into directly-reflected light Q1 (surface-reflected light) that is reflected by the surface of the living body Z1 and internally-reflected light L that is reflected after entering inside the living body Z1. In the first embodiment, the directly-reflected light Q1 is irrelevant to estimation of biological components. Therefore, in the following, the internally-reflected light L will be described. The directly-reflected light Q1 is eliminated by arranging, in front of the optical system 21, a polarizing filter or the like that transmits only light of a predetermined wavelength band. It is of course possible to eliminate components of the directly-reflected light Q1 by image processing or the like. Further, in FIG. 4, it is assumed that the living body Z1 has a two-layer model including a layer A and a layer B for schematic illustration. Furthermore, the layer A includes a substance a, and the layer B includes a substance b. Moreover, in FIG. 4, shading W1 is represented by hatching.

In FIG. 4, the internally-reflected light L (x, y, λ) with a wavelength A at a position (x, y) is given by Equation (1) below using the modifier Lambert-Beer Law.

$$L(x,y,\lambda)=e^{-\rho_A(x,y)\sigma_A(\lambda)l_A(\lambda)-\rho_b(x,y)\sigma_B(\lambda)l_B(\lambda)}E(x,y,\lambda) \quad (1)$$

E(x, y, Δ) represents an irradiation level, $\rho_a$(x, y) represents a concentration of the substance a, $\rho_b$(x, y) represents a concentration of the substance b, $\sigma_a$(x, y) represents an area related to absorption, $\sigma_b$(x, y) represents an area related to absorption, $l_A(\lambda)$ represents an average optical path length of the layer A, and $l_B(\lambda)$ represents an average optical path length of the layer B.

Here, assuming that an imaging signal is represented by $v_i$(x, y) where i=R, G, or B, Equation (2) below is obtained.

$$v_i(x,y)=k\int L(x,y,\lambda)s_i(\lambda)d\lambda=$$
$$k\int e^{-\rho_a(x,y)\sigma_A(\lambda)l_A(\lambda)-\rho_b(x,y)\sigma_B(\lambda)l_B(\lambda)}E x,y,\lambda)s_i(\lambda)d\lambda \quad (2)$$

$s_i(\lambda)$ represents sensitivity (ISO sensitivity) of the imaging apparatus 2, and k represents a coefficient (gain).

For the sake of simplicity, assuming that $s_i(\lambda)=\delta(\lambda-\lambda_i)$, and assuming that $\overline{E}(\lambda)$ is adopted, Equation (3) below is obtained.

$$E(x,y,\lambda)=\rho(x,y)\overline{E}(\lambda) \quad (3)$$

ρ(x, y) represents a shading coefficient.

The imaging signal $v_i$(x, y) is represented as follows based on Equations (2) and (3) described above.

$$v_i(x,y)=ke^{-\rho_a(x,y)\sigma_A(\lambda_i)l_A(\lambda_i)-\rho_b(x,y)\sigma_B(\lambda_i)l_B(\lambda_i)}\rho(x,y)\overline{E}(\lambda_i) \quad (4)$$

Consequently, Equation (5) below is obtained.

$$v^{log}(x,y)=-\rho_a(x,y)\sigma_a-\rho_b(x,y)\sigma_b+\rho^{log}(x,y)1+e^{log} \quad (5)$$

However, the following is obtained.

$$v^{log}(x,y)=[\log v_R(x,y)\log v_G(x,y)\log v_B(x,y)]^T,$$

$$\sigma_a=[\sigma_a(\lambda_R)l_A(\lambda_R)\sigma_a(\lambda_G)l_A(\lambda_G)\sigma_a(\lambda_B)l_A(\lambda_B)]^T,$$

$$\sigma_b=[\sigma_b(\lambda_R)l_B(\lambda_R)\sigma_b(\lambda_G)l_B(\lambda_G)\sigma_b(\lambda_B)l_B(\lambda_B)]^T,$$

$$1=[1\ 1\ 1]^T,$$

$$\rho^{log}(x,y)=\log(\rho(x,y))+\log(k))$$

$$e^{log}(x,y)=[\log E_R(\lambda_R)\log E_G(\lambda_G)\log E_B(\lambda_B)]^T \quad (6)$$

Figure 5:
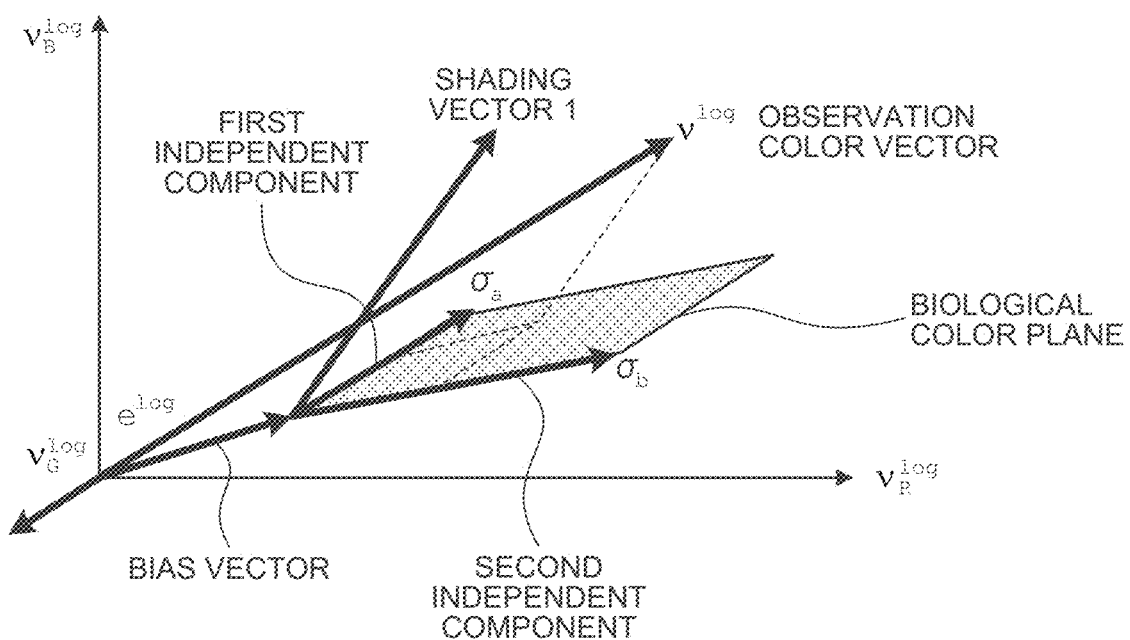
FIG. 5 is a diagram illustrating a relationship of vectors in Equation (6)

FIG. 5 is a diagram illustrating a relationship of vectors in Equation (6). As illustrated in FIG. 5, an RGB signal $v^{log}$ obtained through logarithmic transformation is represented as composition of four vectors $\sigma_a$, $\sigma_b$, 1, and $e^{log}$ (x, y). Further, if a biological color plane is experimentally defined in advance, the biological component distribution estimation unit 541 is able to estimate an ingredient amount (spatial distribution) of each of the substance a (first independent component) and the substance b (second independent component) by projecting a logarithm vector $v^{log}$ of an RGB value of an observation signal along the vector 1 and obtaining values of coefficients in directions of the vectors $\sigma_a$ and $\sigma_b$.

Figure 6A:
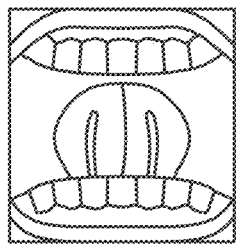
FIG. 6A is a diagram illustrating an example of an image of an input frame of video data input to the image processing apparatus.
Figure 6B:
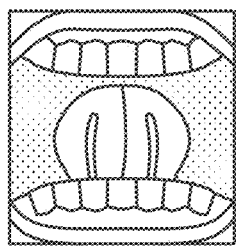
FIG. 6B is a diagram illustrating an example of an image of a shading component.
Figure 6C:
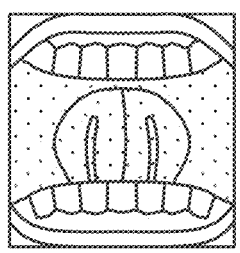
FIG. 6C is a diagram illustrating an example of an image of a first independent component.
Figure 6D:
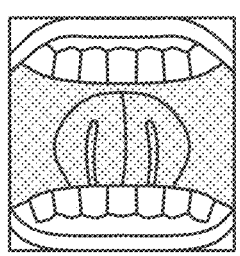
FIG. 6D is a diagram illustrating an example of an image of a second independent component.

FIG. 6A to FIG. 6D are diagrams illustrating examples of images in which components are separated. FIG. 6A is a diagram illustrating an example of an image of an input frame of video data input to the image processing apparatus 5, FIG. 6B is a diagram illustrating an example of an image of a shading component, FIG. 6C is a diagram illustrating an example of an image of the first independent component, and FIG. 6D is a diagram illustrating an example of an image of the second independent component.

As illustrated in FIG. 6A to FIG. 6D, the biological component distribution estimation unit 541 performs the above-described process and eliminates the shading component from the image of the input frame. Accordingly, it is possible to eliminate an influence due to variation of the shading component caused by subtle motions of the subject.

In the above-described model, for example, if it is assumed that the substance a is melanin and the substance b is hemoglobin, the biological component distribution estimation unit 541 is able to extract a hemoglobin component (second independent component). In this case, the biological component extracted by the biological component distribution estimation unit 541 depends on a biological color plane that is generated in advance, and the same effect can be obtained even when any one of hemoglobin, oxygenated hemoglobin, reduced hemoglobin, and bilirubin is extracted.

Further, the component extracted by the biological component distribution estimation unit 541 may be defined as an axis representing a plurality of components, i.e., a combination of two or more of hemoglobin, oxygenated hemoglobin, reduced hemoglobin, and bilirubin. It is of course possible for the biological component distribution estimation unit 541 to separate the biological component (first independent component), such as melanin, cytochrome, and myoglobin, that does not periodically vary and other biological components. The biological component distribution estimation unit 541 may perform the component separation process by using a well-known technique (for example, see Japanese Patent No. 4756398, Wang, W., den Brinker, A., Stuijk, S. and de Haan, G., "Algorithmic principles of remote-PPG," IEEE Trans Biomed Eng 2016 Sep. 13. Epub 2016 Sep. 13., or the like).

Referring back to FIG. 3, explanation of Step S203 and subsequent steps will be continued.

At Step S203, if the process on the image data of all of the frames included in the video data is completed (Step S203: Yes), the image processing apparatus 5 proceeds to Step S204 to be described later. In contrast, if the process on the image data of all of the frames included in the video data is not completed (Step S203: No), the image processing apparatus 5 returns to Step S202 described above, and repeats the process until the component separation process is completed on the image data of all of the frames included in the video data.

At Step S204, the video generation unit 542 performs temporal bandpass filter processing on the biological component video data that is subjected to the component separation process at Step S202, and generates periodic variation video data of the biological component that varies with a desired cycle (Step S204). In general, the heart rate varies with age, but the normal heart rate is 60 beat per minute (bpm). Therefore, the video generation unit 542 generates the periodic variation video data in which a heartbeat variation component as the biological component is extracted, by performing bandpass filter processing on the biological component video data by using a bandpass filter for extracting components that correspond to 0.5 to 3 Hz (30 to 180 bpm) and that include a frequency component of 60 bpm representing the heart rate. Meanwhile, a relationship between the biological component and the frequency characteristic of the bandpass filter is not limited to a one-to-one relationship, but it may be possible to provide a plurality of bandpass filters depending on biological components.

Subsequently, the video generation unit 542 outputs the periodic variation video data of the biological component generated at Step S204 to the recording unit 52 (Step S205). The periodic variation video data output to the recording unit 52 may be displayed as it is on an external display device or may be transferred to and used by other devices. After Step S205, the image processing apparatus 5 returns to Step S102 in FIG. 2 described above.

According to the first embodiment as described above, the biological component distribution estimation unit 541 estimates the spatial distribution of the predetermined biological component for which the component spectrum temporally varies with respect to the image data of a predetermined frame, such as each of frames, among the frames included in the video data, and generates the biological component video data in which the biological component is extracted from the video data based on the estimated spatial distribution of the biological component of the image data of each of the frames, and thereafter, the video generation unit 542 generates the periodic variation video data of the biological component by applying a bandpass filter for extracting a predetermined frequency component to the biological component video data of the biological component that is generated by the biological component distribution estimation unit 541 and that is irrelevant to shading changes; therefore, it is possible to eliminate artifacts caused by variation of the shading component and visually recognize only subtle variation caused by a living body.

Next, a second embodiment will be described. An image processing unit according to the second embodiment has a different configuration from that of the image processing unit 54 according to the first embodiment as described above, and an image processing apparatus performs different processing. In the following, the configuration of the image processing unit according to the second embodiment is first described, and thereafter, the processing performed by the image processing apparatus according to the second embodiment will be described. The same components as those of the imaging system 1 according to the first embodiment as described above are denoted by the same reference symbols, and explanation thereof will be omitted.

Figure 7:
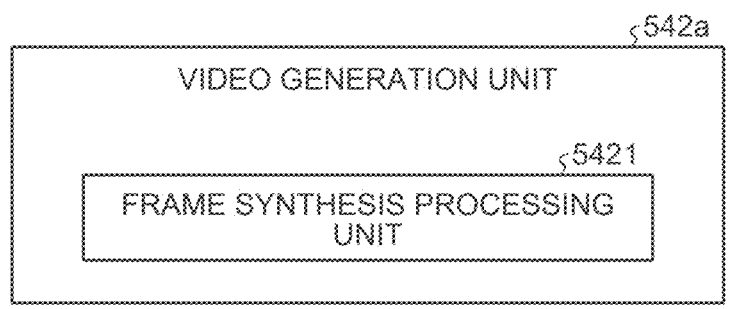
FIG. 7 is a block diagram illustrating a functional configuration of a video generation unit according to a second embodiment.

FIG. 7 is a block diagram illustrating a functional configuration of a video generation unit according to the second embodiment. As illustrated in FIG. 7, the image processing unit 54 includes a video generation unit 542a, instead of the video generation unit 542 according to the first embodiment as described above.

The video generation unit 542a generates periodic variation video data of a biological component by applying, to biological component video data, a filter for extracting a predetermined frequency component. Further, the video generation unit 542a includes a frame synthesis processing unit 5421.

The frame synthesis processing unit 5421 generates emphasized video data in which subtle variation of the biological component is emphasized, by synthesizing the periodic variation video data and the video data in a weighted manner. Specifically, the frame synthesis processing unit 5421 generates the emphasized video data in which the subtle variation of the biological component is emphasized, by synthesizing the periodic variation video data and the video data at a synthesis ratio of 1 to 1. For example, the frame synthesis processing unit 5421 generates the emphasized video data in which the subtle variation of the biological component is emphasized, by synthesizing the periodic variation video data that is multiplied by a weighted coefficient of 0.5 and the video data that is multiplied by a weighted coefficient of 0.5.

Processing Performed by Image Processing Apparatus

Figure 8:
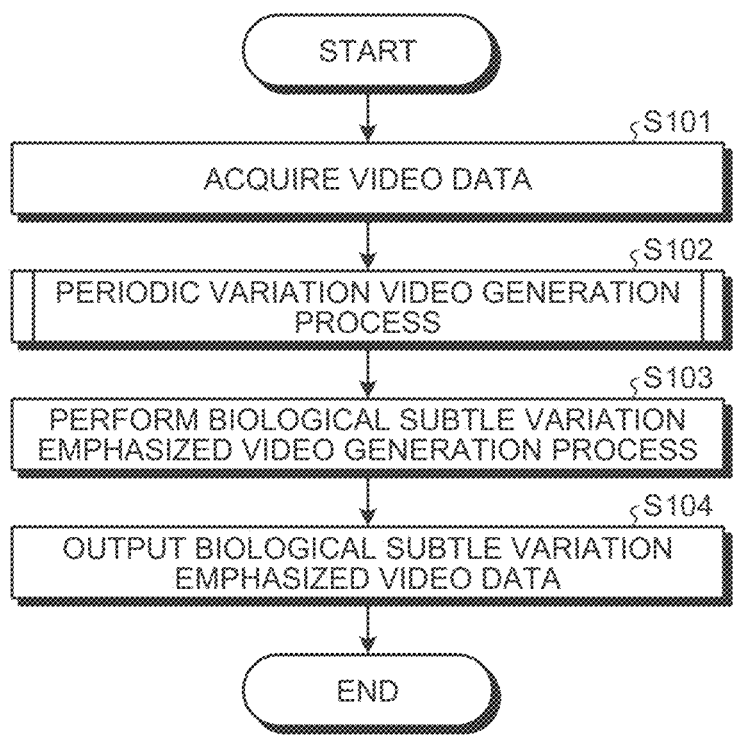
FIG. 8 is a flowchart executed by an image processing apparatus according to the second embodiment.

Next, processing performed by the image processing apparatus 5 will be described. FIG. 8 is a flowchart executed by the image processing apparatus 5. As illustrated in FIG. 8, the image processing apparatus 5 according to the second embodiment further performs processes at Step S103 and Step S104 in addition to the processes at Step S101 and Step S102 of the first embodiment as described above. Therefore, in the following, Step S103 and Step S104 will be described.

At Step S103, the frame synthesis processing unit 5421 performs a biological subtle variation emphasized video generation process of generating the emphasized video data in which biological subtle variation is emphasized, by causing the biological component distribution estimation unit 541 to synthesize the periodic variation video data and the video data generated in a weighted manner.

Subsequently, the frame synthesis processing unit 5421 outputs the biological subtle variation emphasized video data generated at Step S103 to the display unit 4 (Step S104). Meanwhile, the process at Step S104 is not always needed, and, the image processing apparatus 5 is able to select whether to perform this process depending on operation on the input unit 3 and it may be possible to display the video data as it is on the external display unit 4 or transfer and use the video data to and in other devices. After Step S104, the image processing apparatus 5 terminates the process.

Here, an emphasized video corresponding to the emphasized video data displayed by the display unit 4 will be described. FIG. 9A to FIG. 9D are diagrams schematically illustrating examples of a video corresponding to original video data generated by the imaging apparatus 2. FIG. 10A to FIG. 10D are diagrams schematically illustrating examples of a video corresponding to video data obtained by the conventional video magnification method. FIG. 11A to FIG. 11D are diagrams schematically illustrating examples of the emphasized video corresponding to the emphasized video data according to the second embodiment, and schematically illustrating examples of the emphasized video in which the first independent component is emphasized as the biological component. In FIG. 10A to FIG. 10D, shaded portions are represented by hatching. Further, in FIG. 11A to FIG. 11D, emphasized portions are represented by hatching. Meanwhile, in FIG. 9A to FIG. 9D, FIG. 10A to FIG. 10D, and FIG. 11A to FIG. 11D, veins (sublingual choroid) on the back side of tongue in an oral cavity is schematically illustrated.

Figure 9A:
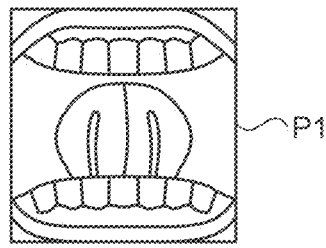
FIG. 9A is a diagram schematically illustrating an example of a video corresponding to original video data generated by an imaging apparatus.
Figure 9B:
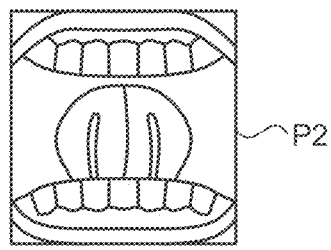
FIG. 9B is a diagram schematically illustrating an example of the video corresponding to the original video data generated by the imaging apparatus.
Figure 9C:
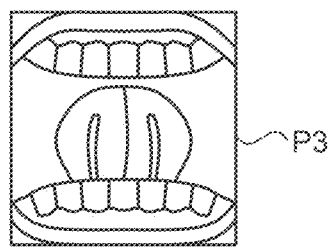
FIG. 9C is a diagram schematically illustrating an example of the video corresponding to the original video data generated by the imaging apparatus.
Figure 9D:
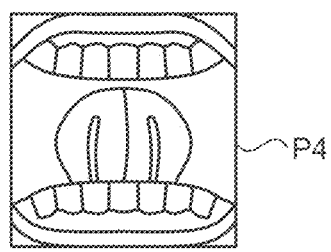
FIG. 9D is a diagram schematically illustrating an example of the video corresponding to the original video data generated by the imaging apparatus.
Figure 10A:
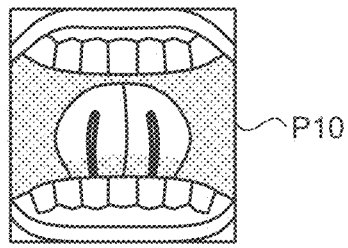
FIG. 10A is a diagram schematically illustrating an example of a video corresponding to video data using a conventional video magnification method.
Figure 10B:
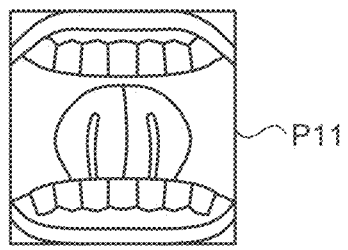
FIG. 10B is a diagram schematically illustrating an example of the video corresponding to the video data obtained by the conventional video magnification method.
Figure 10C:
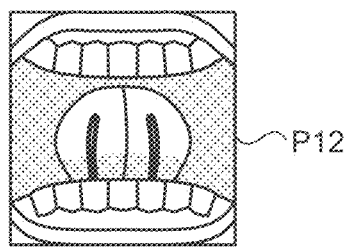
FIG. 10C is a diagram schematically illustrating an example of the video corresponding to the video data obtained by the conventional video magnification method.
Figure 10D:
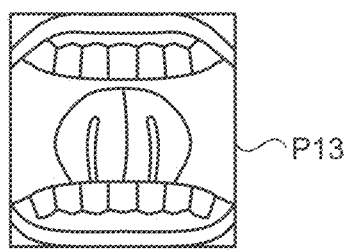
FIG. 10D is a diagram schematically illustrating an example of the video corresponding to the video data obtained by the conventional video magnification method.

As indicated by an image P1 to an image P4 in FIG. 9A to FIG. 9D, it is difficult to visually recognize variation caused by heartbeat (variation of sublingual choroid) in the original video (FIG. 9A→FIG. 9B→FIG. 9C→FIG. 9D). Further, as indicated by an image P10 to an image P13 in FIG. 10A to FIG. 10D, in the conventional method, the entire images are darkened depending on frames (FIG. 10A→FIG. 10B→FIG. 10C→FIG. 10D). In the conventional method, because RGB signals included in the image data are emphasized, variation of the shading component is emphasized (for example, the image P10 in FIG. 10A and the image P12 in FIG. 10C). Therefore, it is difficult to visually recognize variation caused by heartbeat (variation of sublingual choroid).

Figure 11A:
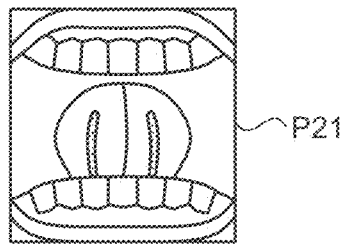
FIG. 11A is a diagram schematically illustrating an example of an emphasized video corresponding to emphasized video data according to the second embodiment.
Figure 11B:
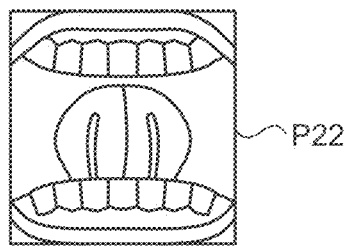
FIG. 11B is a diagram schematically illustrating an example of the emphasized video corresponding to the emphasized video data according to the second embodiment.
Figure 11C:
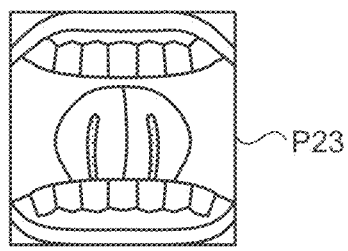
FIG. 11C is a diagram schematically illustrating an example of the emphasized video corresponding to the emphasized video data according to the second embodiment.
Figure 11D:
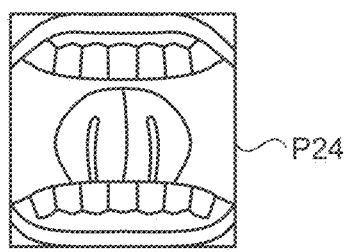
FIG. 11D is a diagram schematically illustrating an example of the emphasized video corresponding to the emphasized video data according to the second embodiment.

In contrast, in the second embodiment, as indicated by images P21 to P24 in FIG. 11A to FIG. 11D, it is possible to eliminate artifacts caused by variation of the shading component and emphasize periodic variation at only blood vessel positions (variation of sublingual choroid is represented by hatching) (FIG. 11A→FIG. 11B→FIG. 11C→FIG. 11D). This is because it is possible to eliminate the shading component by component separation of biological components, and emphasize only a desired biological component (second independent component).

According to the second embodiment as described above, the frame synthesis processing unit 5421 generates the emphasized video data in which subtle variation of the biological component is emphasized by synthesizing the periodic variation video data and the video data in a weighted manner, and outputs the emphasized video data to the display unit 4; therefore, it is possible to eliminate shading changes (for example, changes of irregularity or changes of a surface shape) that are caused by motions of the subject or illumination variation (intensity or irradiation direction), and enhance and display only local variation caused by the living body, so that is possible to easily and visually recognize presence or absence of blood vessels in a surface layer of the living body.

Meanwhile, in the second embodiment, the frame synthesis processing unit 5421 generates the emphasized video data in which a temporal change of hemoglobin is emphasized by synthesizing the periodic variation video data and the video data in a weighted manner at an equal synthesis ratio, but embodiments are not limited thereto, and the frame synthesis processing unit 5421 may synthesize the periodic variation video data and the video data in a weighted manner while changing the synthesis ratio in accordance with weighting coefficients corresponding to an instruction signal input from the input unit 3. For example, the frame synthesis processing unit 5421 may generate the emphasized video data in which only a temporal change of a hemoglobin component (second independent component) is emphasized by synthesizing the periodic variation video data and the video data such that the weighting coefficient of the periodic variation video data is set to 1.

Furthermore, while the frame synthesis processing unit 5421 synthesizes the periodic variation video data and the video data in the second embodiment, it may be possible to generate the emphasized video data in which local and subtle variation of two biological components is emphasized by synthesizing, in a weighted manner, periodic variation video data in which a biological component different from the hemoglobin component is extracted and periodic variation video data in which the hemoglobin component is extracted, instead of synthesizing the video data, and output the emphasized video data to the display unit 4.

Next, a third embodiment will be described. An image processing unit according to the third embodiment has a different configuration from that of the image processing unit 54 according to the first embodiment as described above, and an image processing apparatus performs different processing. In the following, the configuration of the image processing unit according to the third embodiment is first described, and thereafter, the processing performed by the image processing apparatus according to the third embodiment will be described. The same components as those of the imaging system 1 according to the first embodiment as described above are denoted by the same reference symbols, and explanation thereof will be omitted.

Figure 12:
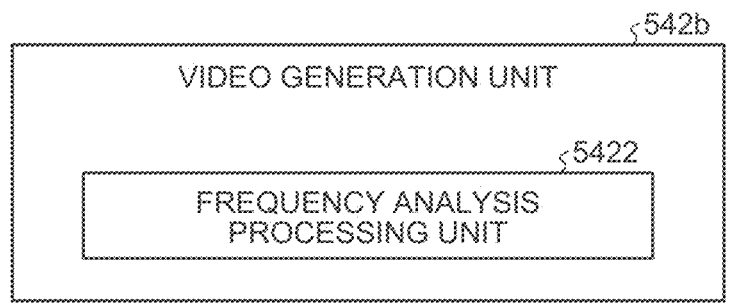
FIG. 12 is a block diagram illustrating a functional configuration of a video generation unit according to a third embodiment.

FIG. 12 is a block diagram illustrating a functional configuration of a video generation unit according to the third embodiment. As illustrated in FIG. 12, the image processing unit 54 includes a video generation unit 542b, instead of the video generation unit 542 according to the first embodiment as described above.

The video generation unit 542b generates periodic variation video data of a biological component by applying, to biological component video data, a filter for extracting a predetermined frequency component. Further, the video generation unit 542b includes a frequency analysis processing unit 5422.

The frequency analysis processing unit 5422 performs frequency analysis on temporal variation at a predetermined position (video position) in image data of each of frames with respect to the periodic variation video data, generates display image data in which at least one of a luminance value and a color is set based on at least one of amplitude of a predetermined frequency component and magnitude of a power spectrum of the predetermined frequency component, and outputs the display image data to the display unit 4.

Processing Performed by Image Processing Apparatus

Figure 13:
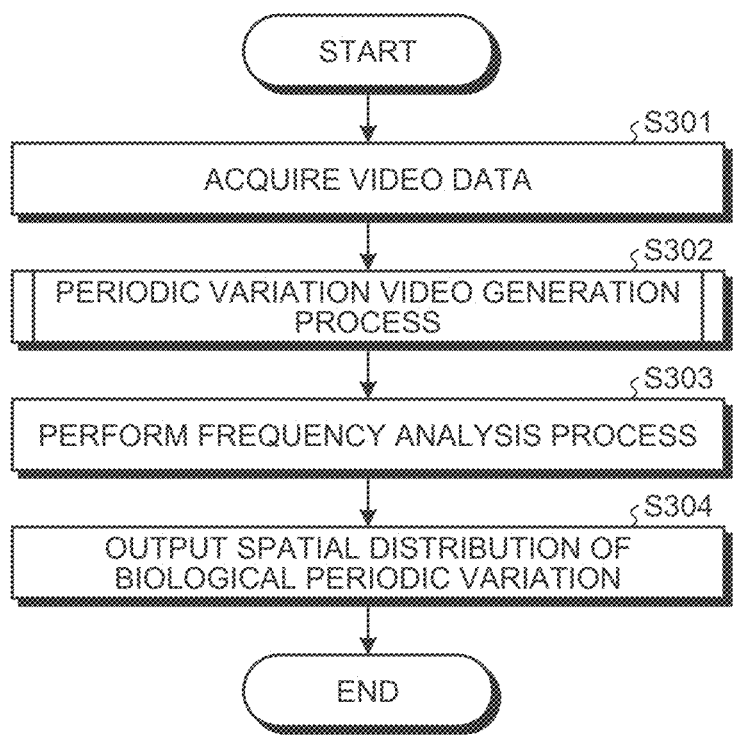
FIG. 13 is a flowchart executed by an image processing apparatus according to the third embodiment.

FIG. 13 is a flowchart illustrating an outline of the processing performed by the image processing apparatus 5. In FIG. 13, Step S301 and Step S302 respectively correspond to Step S101 and Step S102 in FIG. 2 described above.

At Step S303, the frequency analysis processing unit 5422 performs a frequency analysis process of inputting the periodic variation video data of the biological component and outputting a spatial distribution of the biological periodic variation. After Step S303, the image processing apparatus 5 proceeds to Step S304 to be described later.

Figure 14:
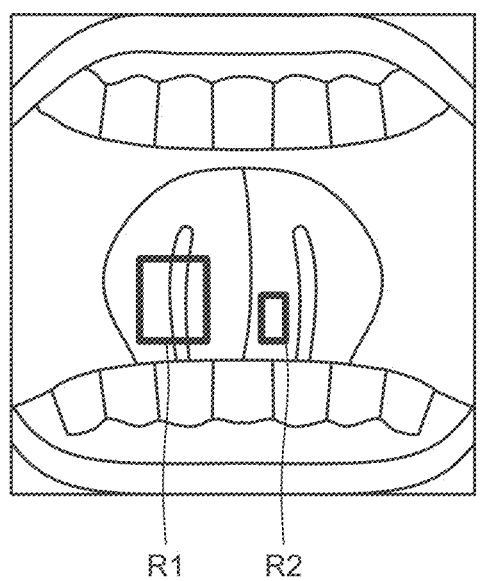
FIG. 14 is a diagram illustrating an example of an image of one frame of a periodic variation video of a biological component for which a frequency analysis processing unit according to the third embodiment performs frequency analysis.

FIG. 14 is a diagram illustrating an example of an image of one frame of a periodic variation video of a biological component for which the frequency analysis processing unit 5422 performs frequency analysis. In the third embodiment, the frequency analysis processing unit 5422 performs the frequency analysis on a region R1 and a region R2 illustrated in FIG. 14. Meanwhile, the region R1 includes a vein (sublingual choroid) on the back side of tongue in an oral cavity.

Figure 15A:
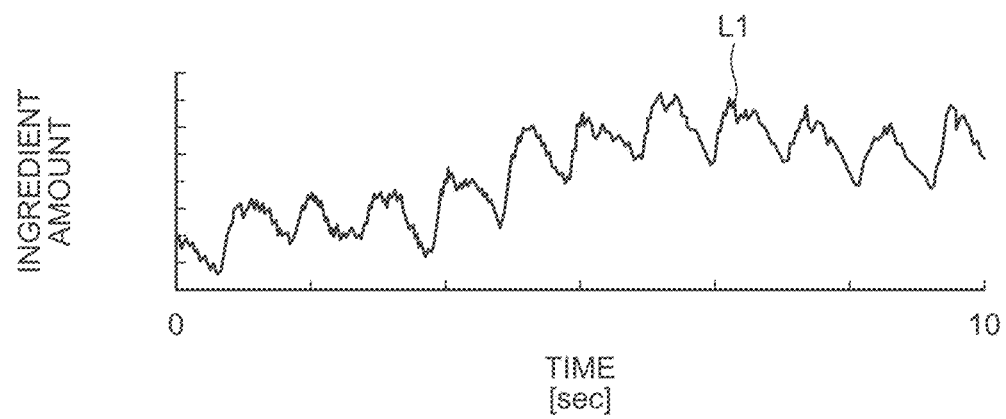
FIG. 15A is a diagram illustrating temporal variation of a biological component value of a periodic variation video of the biological component in a region R1 illustrated in FIG. 14.
Figure 15B:
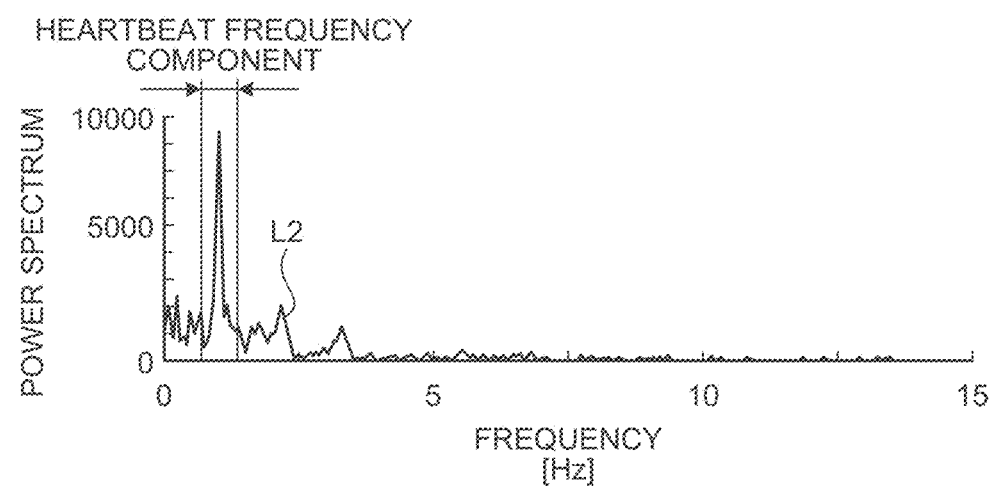
FIG. 15B is a diagram illustrating a frequency analysis result of the temporal variation of the biological component value in the region R1 illustrated in FIG. 14.
Figure 16A:
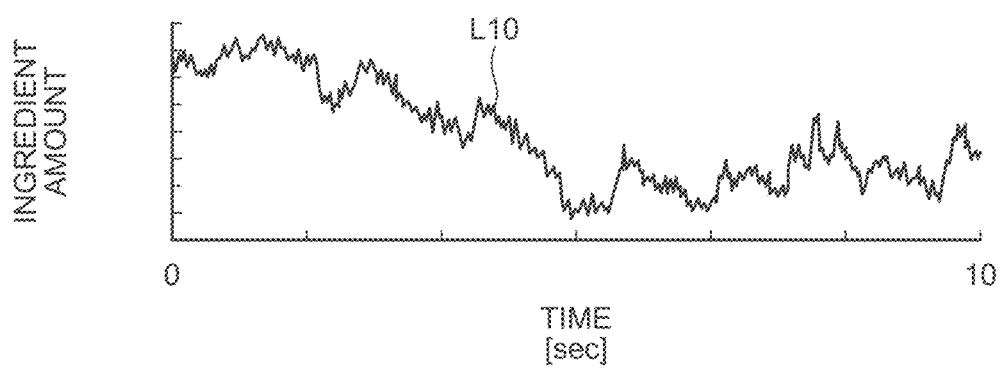
FIG. 16A is a diagram illustrating temporal variation of the biological component value of the periodic variation video of the biological component in a region R2 illustrated in FIG. 14.
Figure 16B:
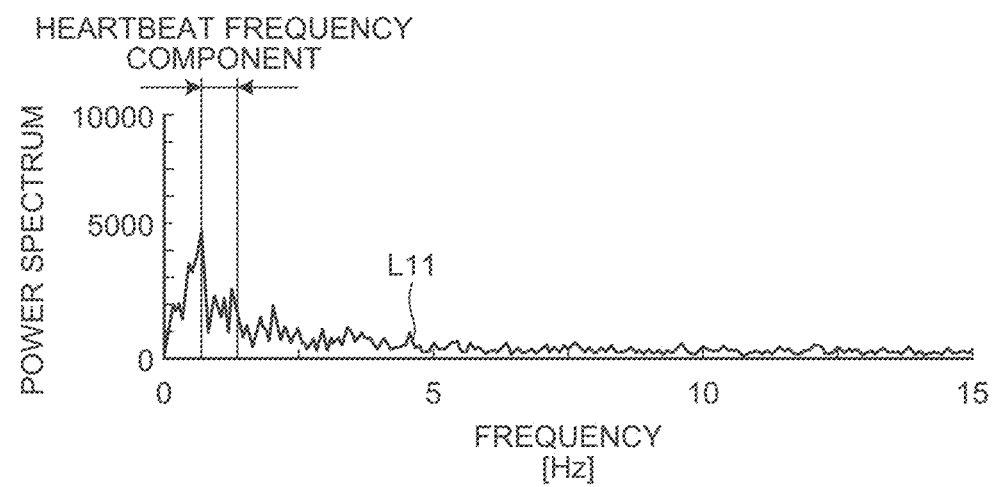
FIG. 16B is a diagram illustrating a frequency analysis result of the temporal variation of the biological component value in the region R2 illustrated in FIG. 14.
Figure 17:
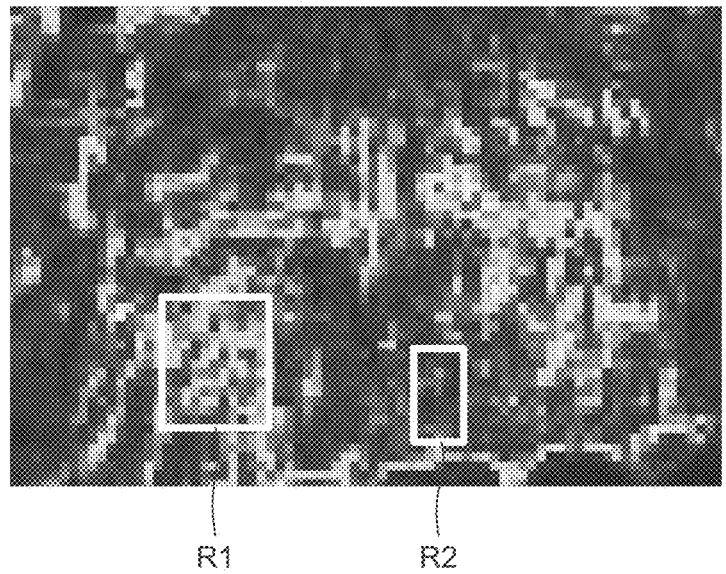
FIG. 17 is a diagram illustrating an example of a spatial distribution of biological periodic variation.

Further, FIG. 15A and FIG. 15B are diagrams illustrating temporal variation of a biological component value of the periodic variation video of the biological component in the region R1 illustrated in FIG. 14 and a frequency analysis result of the temporal variation of the biological component value. FIG. 16A and FIG. 16B are diagrams illustrating temporal variation of the biological component value of the periodic variation video of the biological component in the region R2 illustrated in FIG. 14 and a frequency analysis result of the temporal variation of the biological component value. FIG. 17 is a diagram illustrating an example of a spatial distribution of biological periodic variation. In FIG. 15A and FIG. 16A, horizontal axes represent time (sec), vertical axes represent an ingredient amount, a curve L1 represents the temporal variation of the biological component value in the region R1, and a curve L10 represents the temporal variation of the biological component value in the region R2. In FIG. 15B and FIG. 16B, a curve L2 represents the frequency analysis result of the temporal variation of the biological component value in the region R1, and a curve L11 represents the frequency analysis result of the temporal variation of the biological component value in the region R2.

As illustrated in FIG. 15A, in the region R1, the component value periodically varies due to heartbeat. In contrast, as illustrated in FIG. 16A, in the region R2, the component value does not periodically vary due to heartbeat. Specifically, as illustrated in FIG. 15B, in the region R1, a value of the power spectrum of the region R1 is large at around 1 Hz that represents a heartbeat frequency component. In contrast, as illustrated in FIG. 16B, in the region R2, a value of the power spectrum of the region R2 is small at around 1 Hz that represents a heartbeat frequency component. As illustrated in FIG. 17, the frequency analysis processing unit 5422 calculates integral values of the power spectrum of a heartbeat frequency region that is a desired frequency component as described above, and generates a heat map (display image data) in which colors are added in accordance with the integral values of the power spectrum. Specifically, the frequency analysis processing unit 5422 generates the heat map such that red is applied to large integral values of the power spectrum and blue is added to small integral values (red>yellow>blue). Consequently, it is possible to visualize the spatial distribution of the local and subtle variation caused by heartbeat.

Referring back to FIG. 13, explanation of Step S304 and subsequent steps will be given below.

At Step S304, the frequency analysis processing unit 5422 outputs the spatial distribution of the biological periodic variation, which is generated by performing the frequency analysis process on the periodic variation video of the biological component, to the display unit 4. Meanwhile, the process at Step S304 is not always needed, and, the image processing apparatus 5 is able to select whether to perform this process depending on operation on the input unit 3 and it may be possible to display the video data as it is on the external display unit 4 or transfer and use the video data to and in other devices. After Step S304, the image processing apparatus 5 terminates the process.

According to the third embodiment as described above, the frequency analysis processing unit 5422 performs the frequency analysis on the temporal variation at the predetermined position in the image data of each of the frames with respect to the periodic variation video data, generates the heat map in which colors are set based on at least one of the amplitude of the predetermined frequency component and the magnitude of the power spectrum of the predetermined frequency component, and outputs the heat map to the display unit 4; therefore, it is possible to output the spatial distribution of at least one of the amplitude and the power spectrum of the desired frequency component, so that it is possible to visualize the spatial distribution of subtle variation caused by heartbeat, where the variation can hardly be visually recognized in the original video, and it is possible to provide auxiliary information for estimating presence or absence of a blood vessel that exists in a layer below the biological surface.

Meanwhile, in the third embodiment, the frequency analysis processing unit 5422 may perform the frequency analysis on the temporal variation at the predetermined position in the image data of each of the frames with respect to the periodic variation video data, generate a histogram based on at least one of the amplitude of the predetermined frequency component and the magnitude of the power spectrum of the predetermined frequency component, and output the histogram to the display unit 4. It is of course possible for the frequency analysis processing unit 5422 to generate display image data in which the luminance value is emphasized based on at least one of the amplitude of the predetermined frequency component and the magnitude of the power spectrum of the predetermined frequency component, and output the display image data to the display unit 4.

Next, a fourth embodiment will be described. An image processing unit according to the fourth embodiment has a different configuration from the image processing unit 54 according to the first embodiment as described above, and an image processing apparatus performs different processing. In the following, the configuration of the image processing unit according to the fourth embodiment is first described, and thereafter, the processing performed by the image processing apparatus according to the fourth embodiment will be described. The same components as those of the imaging system 1 according to the first embodiment as described above are denoted by the same reference symbols, and explanation thereof will be omitted.

Figure 18:
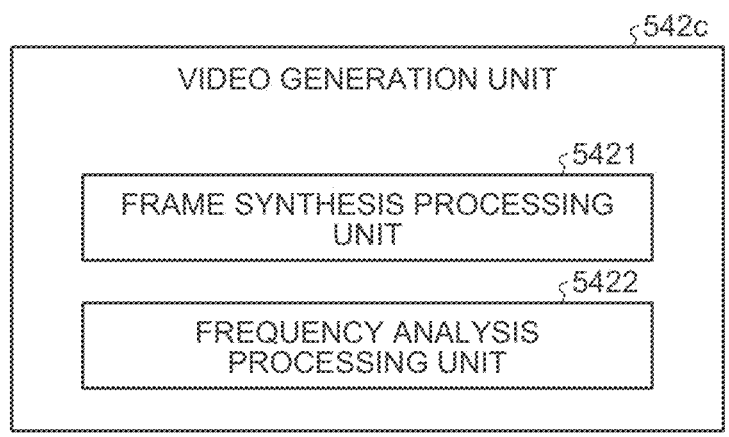
FIG. 18 is a block diagram illustrating a functional configuration of a video generation unit according to a fourth embodiment.

FIG. 18 is a block diagram illustrating a functional configuration of a video generation unit according to the fourth embodiment. As illustrated in FIG. 18, the image processing unit 54 includes a video generation unit 542c, instead of the video generation unit 542 according to the first embodiment as described above.

The video generation unit 542c generates periodic variation video data of a biological component by applying, to biological component video data, a filter for extracting a predetermined frequency component. Further, the video generation unit 542c includes the frame synthesis processing unit 5421 and the frequency analysis processing unit 5422 as described above.

Figure 19:
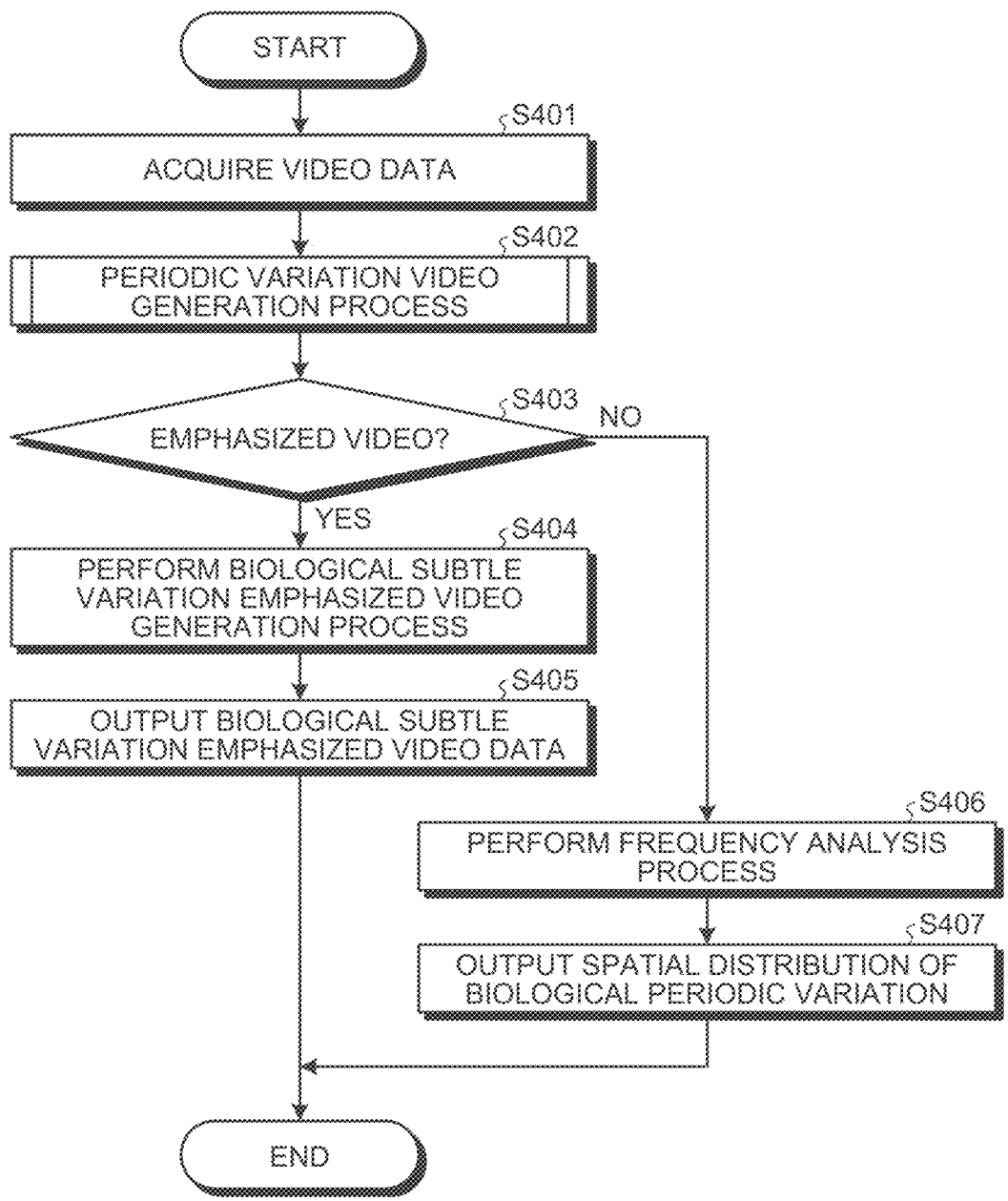
FIG. 19 is a flowchart illustrating an outline of processing performed by an image processing apparatus according to the fourth embodiment.

FIG. 19 is a flowchart illustrating an outline of the processing performed by the image processing apparatus 5. In FIG. 19, Step S401 and Step S402 respectively correspond to Step S101 and Step S102 in FIG. 2 described above.

At Step S403, if the input unit 3 inputs an instruction signal for displaying the emphasized video (Step S403: Yes), the image processing apparatus proceeds to Step S404 to be described below. In contrast, if the input unit 3 does not input the instruction signal for displaying the emphasized video (Step S403: No), the image processing apparatus proceeds to Step S406 to be described below.

Step S404 and Step S405 respectively correspond to Step S103 and Step S104 in FIG. 8 described above. Meanwhile, the process at Step S405 is not always needed, and, the image processing apparatus 5 is able to select whether to perform this process depending on operation on the input unit 3 and it may be possible to display the video data as it is on the external display unit 4 or transfer and use the video data to and in other devices. After Step S405, the image processing apparatus 5 terminates the process.

Step S406 and Step S407 respectively correspond to Step S303 and Step S304 in FIG. 13 described above. The process at Step S407 is not always needed, and, the image processing apparatus 5 is able to select whether to perform this process depending on operation on the input unit 3 and it is possible to display the video data as it is on the external display unit 4 or transfer and use the video data to and in other devices. After Step S407, the image processing apparatus 5 terminates the process.

According to the fourth embodiment of the present disclosure as described above, it is possible to display, on the display unit 4, the emphasized video data or the display image data that represents the spatial distribution of at least one of the amplitude of the desired frequency component and the magnitude of the power spectrum of the desired frequency component depending on operation on the input unit 3.

Meanwhile, while one of the emphasized video data and the display image data that represents the spatial distribution of at least one of the amplitude of the desired frequency component and the magnitude of the power spectrum of the desired frequency component is output to the display unit 4 depending on operation on the input unit 3 in the fourth embodiment, embodiments are not limited to this example, and it may be possible to output each of the emphasized video data and the display image data to the display unit 4.

In the first to the fourth embodiments, the imaging system includes each of the imaging apparatus, the input unit, the display unit, the recording unit, and the control unit, but these components may be removed without departing from the spirit or scope of the present disclosure. Furthermore, variations may be made by appropriately combining a plurality of components disclosed in the first to the fourth embodiments described above. For example, some of the components may be removed from all of the components illustrated in the first to the fourth embodiments described above. Moreover, the components illustrated in the first to the fourth embodiments described above may be appropriately combined.

Furthermore, while each of the imaging apparatus, the input unit, and the display unit is separated from the image processing apparatus in the first to the fourth embodiments described above, they may be integrated with one another.

Moreover, in the present embodiments, "a unit" described above may be replaced with "a means", "a circuit", or the like. For example, the control unit may be replaced with a control means or a control circuit.

Furthermore, in the present embodiments, the video data is transmitted from the imaging apparatus to the image processing apparatus via a transmission cable, but the transmission need not always be performed in a wired manner and may be performed in a wireless manner. In this case, it is sufficient to transmit video data or the like from the imaging apparatus to the image processing apparatus in accordance with a predetermined wireless communication standard (for example, Wi-Fi (registered trademark) or Bluetooth (registered trademark)). It is of course possible to perform wireless communication based on other wireless communication standards.

Moreover, while the imaging system is used in the present embodiments, it may be possible to adopt a flexible or rigid endoscope to be inserted in a subject, a capsule endoscope, a video microscope that captures images of a subject, a mobile phone having an imaging function, and a tablet terminal having an imaging function.

In describing the flowcharts in this specification, context of the processes is described by using expressions such as "first", "thereafter", "subsequently", and the like, but the sequences of the processes necessary for carrying out the present disclosure are not uniquely defined by these expressions. In other words, the sequences of the processes in the flowcharts described in the present specification may be modified as long as there is no contradiction.

According to the present disclosure, it is possible to reduce influence due to shading variation, and visually recognize variation caused by a living body.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor comprising hardware, the processor being configured to:
acquire video data;
estimate a spatial distribution of a predetermined biological component for which a component spectrum temporally varies with respect to image data of multiple frames of a plurality of frames included in the video data;
generate biological component video data in which the biological component is extracted from the video data based on the estimated spatial distribution of the biological component for which the component spectrum temporally varies in the image data of the multiple frames; and
generate temporal periodic variation video data of the biological component by applying, to the biological component video data, a filter for extracting a periodic variation component including a predetermined frequency.

2. The image processing apparatus according to claim 1, wherein the processor is further configured to generate emphasized video data in which subtle variation of the biological component is emphasized, by synthesizing the temporal periodic variation video data and the video data in a weighted manner.

3. The image processing apparatus according to claim 1, wherein the processor is further configured to:
perform frequency analysis of temporal variation at a predetermined position in the image data of the multiple frames with respect to the temporal periodic variation video data;
generate display image data in which at least one of a luminance value and a color is set based on at least one of an amplitude of the periodic variation component and a magnitude of a power spectrum of the periodic variation component; and
output the display image data.

4. The image processing apparatus according to claim 1, wherein the biological component is at least one of hemoglobin, oxygenated hemoglobin, reduced hemoglobin, and bilirubin.

5. The image processing apparatus according to claim 1, wherein the biological component is a biological component other than melanin, cytochrome, and myoglobin.

6. An image processing method comprising:
acquiring video data;
estimating a spatial distribution of a predetermined biological component for which a component spectrum temporally varies with respect to image data of multiple frames of a plurality of frames included in the video data;

generating biological component video data in which the biological component is extracted from the video data based on the estimated spatial distribution of the biological component for which the component spectrum temporally varies in the image data of the multiple frames; and generating temporal periodic variation video data of the biological component by applying, to the biological component video data, a filter for extracting a periodic variation component including a predetermined frequency.

7. A non-transitory computer-readable recording medium with an executable program stored thereon, the program causing a processor to execute processes comprising:

acquiring video data;

estimating a spatial distribution of a predetermined biological component for which a component spectrum temporally varies with respect to image data of multiple frames of a plurality of frames included in the video data;

generating biological component video data in which the biological component is extracted from the video data based on the estimated spatial distribution of the biological component for which the component spectrum temporally varies in the image data of the multiple frames; and generating temporal periodic variation video data of the biological component by applying, to the biological component video data, a filter for extracting a periodic variation component including a predetermined frequency.

8. The image processing apparatus according to claim 1, wherein the predetermined frequency is a frequency component representing a cyclical variation in a living subject from which the video data is acquired.

* * * * *